United States Patent [19]

Hennig

[11] 4,209,009
[45] Jun. 24, 1980

[54] ANUS CLOSURE TAMPON AND METHOD OF MANUFACTURE

[76] Inventor: Gerhard Hennig, Ammerseestrasse 28, D-8035 Gauting 2, Fed. Rep. of Germany

[21] Appl. No.: 906,946

[22] Filed: May 16, 1978

[30] Foreign Application Priority Data

May 17, 1977 [DE] Fed. Rep. of Germany ....... 2722286

[51] Int. Cl.² ............................................. A61B 19/00
[52] U.S. Cl. .................................. 128/1 R; 128/283; 128/270; 128/DIG. 25
[58] Field of Search .............. 128/283, 1 A, 1 R, 270, 128/285, 263, 341

[56] References Cited

U.S. PATENT DOCUMENTS

| 1,561,020 | 11/1925 | Pond | 128/270 |
| 2,149,053 | 2/1939 | Hollister | 128/283 |
| 2,553,382 | 5/1951 | Riordan | 128/270 |
| 2,931,353 | 4/1960 | Kitzul | 128/1 R |
| 3,508,548 | 4/1970 | Hochstrasser et al. | 128/283 |
| 3,528,419 | 9/1970 | Joechle | 128/270 |
| 3,952,726 | 4/1976 | Hennig et al. | 128/283 |
| 3,958,556 | 5/1976 | Schenk | 128/1 R |

FOREIGN PATENT DOCUMENTS 877473 9/1942 France ...................... 128/285

Primary Examiner—John D. Yasko
Attorney, Agent, or Firm—Frishauf, Holtz, Goodman & Woodward

[57] ABSTRACT

To provide reliable holding of a closure tampon for incontinent natural anus or an artificial anus after colostomy, an elongated essentially cylindrical body of cellular material, for example similar to a catamenial tampon, is provided with non-homogeneous sections, taken in longitudinal direction, and having differential diametrical compressibility, so that a section of low compressibility can be inserted in the exit opening for internal expansion to thereby hold its position in the artificial anus, the section of high compressibility permitting constriction to provide, after insertion of the low-compressibility section first, a plug effect.

13 Claims, 4 Drawing Figures

ANUS CLOSURE TAMPON AND METHOD OF MANUFACTURE

Reference to prior patent: U.S. Pat. No. 3,958,556, SCHENK

Reference to prior application: Ser. No. 801,326, filed May 27, 1977, HENNIG et al now U.S. Pat. No. 4,154,226.

The present invention relates to a medical device, and more specifically to a closure tampon for a natural or an artificial anus constructed, for example, by colostomy.

BACKGROUND AND PRIOR ART

Various types of closure arrangements and devices for an artifical excretory opening have been proposed. Such openings are surgically constructed after operations for cancer of the colon extending, for example, through the abdominal wall. Some devices of this type use magnets to hold closure plugs in place (see German Patent Disclosure Documents DE-OS Nos. 23 63 563; 24 47 682; 26 25 243; 27 17 608; U.S. Ser. No. 801,326. In such arrangements, a ring-shaped permanent magnet is implanted in the abdominal wall surrounding the colon in the vicinity of the exit opening. Magnetic closure arrangements then cooperate with the magnet implanted in the abdominal wall. One such arrangement may include a closure cover. Such arrangements have found acceptance, but still require improvement; if, for example, the patient is obese, or the colon is led downwardly at an inclination with respect to the abdominal wall, difficulties may arise. Magnetic closure arrangements have also been proposed in which a rubbery elastic material is used which has a sealing surface, matched to the shape of the region surrounding the excretory opening of the colon. Such arrangements are difficult to fit and must be individually made to fit the particular patient involved.

In another arrangements, an elongated essentially rod-shaped magnetic core is used, surrounded by a cover of soft elastic material such as, for example, foam rubber, foamed plastic, or the like.

Non-magnetic tampons, similar to the customary catamenial tampons, have also been proposed to close excretory openings. Such tampons have not proved suitable since a reliable seat and closure effect cannot be ensured since there is no force, such as the magnetic force above referred to, which tends to hold the tampon in the final portion of the colon. Such simple, non-magnetic closure plugs would, however, have the advantage that the comparatively expensive magnets can be omitted and the entire closure plug could be made so inexpensively that it can be considered a disposal item, to be disposed of after single use. The troublesome and rather disagreeable cleaning of the permanent-type tampons can then be avoided.

THE INVENTION

It is an object to provide a preferably single-use disposable tampon for closing of an excretory opening, which provide for a reliable seat and assured closure of the opening.

Briefly, an elongated, essentially cylindrical body is provided which, in it longitudinal direction, has sections of differential diametrical compressibility or expandability upon wetting and/or warming up by the heat of the human body. A section of low compressibility is, for example, at one end which preferably is also somewhat pointed for ease of insertion, followed by a section of high compressibility so that, upon insertion of the low-compressibility section, the higher compressible section can contract against the force of the customarily implanted holding ring surrounding the excretory opening, thus providing for reliable seating of the tampon in the opening.

In use, the tampon will obtain a non-homogenous diameter, with respect to its length. In use, it will have a longitudinal portion which is thinner than one or two adjacent longitudinal portions. The tampon, initially, may be of essentially uniform thickness, but the differential compressibility, in diametrical direction, will cause the tampon to assume a somewhat hourglass-like shape and thus cause locking of the tampon by the inner, thicker portion within the section of the colon adjacent the artificial ends. The thinner portion, that is, the portion which can compress and thus can become thinner in use is not the end portion to facilitate introduction; rather, it is beyond the end portion, that is, towards the outside of the body of the user.

In accordance with a preferred embodiment of a tampon, at least two longitudinal portions are provided which have low compressibility or high expansion capability so that, in use, they will have thickened cross section, separated from each other by a thinner longitudinal section to result in a somewhat hour-glass-line shape in a simple form.

Material suitable for the tampon is compressed cellular or cellulose-based material, for example of the type generally suitable for catamenial tampons; the portions of differential compressibility can be made of differential compression in manufacture, introducing different quantities of material, or by introducing a core which may have enlarged ends; this core is preferably non-magnetic and may, likewise, have somewhat hourglass-like shape. The tampon and/or the core, preferably, are arranged to provide a duct through which intestinal gases can escape; the duct, preferably, includes, or passes through, granular absorbent material, such as activated charcoal.

Drawings, illustrating preferred examples:

Figure 1:
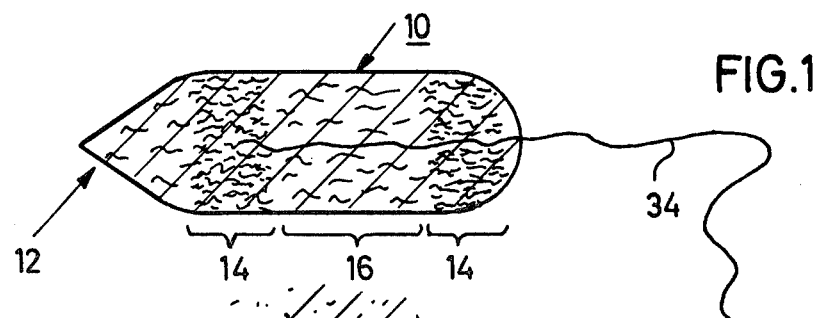
FIG. 1 is a schematic longitudinal section through a tampon of the present invention before use.

An elongated tampon 10 (FIG. 1), which is an essentially cylindrical longitudinal body, is shaped to have a pointed forward end 12. The tampon is made of compressed cellular cellulose material, for example of the type well known for catamenial tampons. In longitudinal direction, the tampon is non-homogeneous. It has two longitudinal sections 14 of low compressibility and high expansion capability, separated by an intermediate section 16 which can be thinner, but generally will be of a material of high compressibility and substantially lesser expansion characteristics than the sections 14. The material, as known, can expand when wetted. In use, the tampon 10 is moistened, for example upon introduction into an artificial anus 18 (FIG. 2). The sections 14 will then expand more than the immediate section 16 so that the overall shape of the tampon will be somewhat to that of an hourglass, that is, centrally constricted. This results in a plug-closing by the expanded tampon 10' (FIG. 2) of the artificial anus opening 18, ensuring reliable closing and seating of the tampon 10'. Preferably, the exit opening of the colon is surrounded by an implanted toroidal support body 20 made of biologically acceptable plastic material. Such a support ring 20 contributes to the reliability of seating of the tampon 10'. The ring 20 does not include magnetic material and may be made internally of suitable plastic material and at the outside, at least, with a plastic which is biologically compatible with tissue, such polyoxymethylene (POM). A string 34 is attached to the tampon for easy removal.

Figure 2:
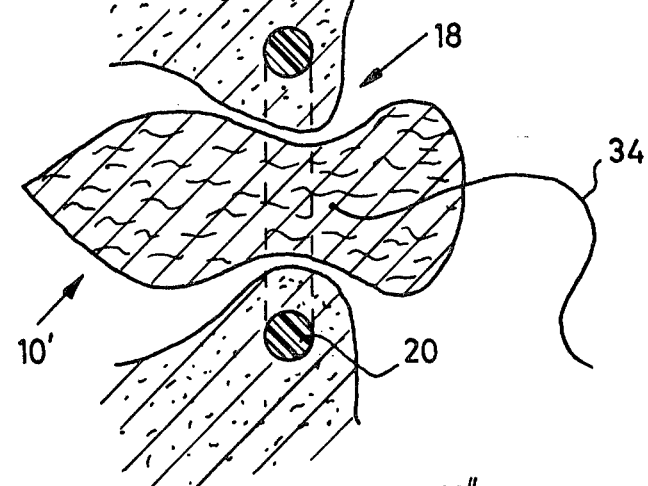
FIG. 2 is a schematic showing of the tampon of FIG. 1, introduced into an artificial anus.

The tampon shown in FIGS. 1 and 2 has two zones 14 and a single intermediate zone 16; it may, however, have more than one intermediate zone, for example three zones 14 with two zones 16 therebetween. Generally, a lesser expanding and/or or higher compressible section 16 will be located between sections of low compressibility and high expansion. If a tampon having, for example, two sections 16 sandwiched between respective sections 14, then high pressure tending to drive the tampon outwardly will tend to move the tampon one section at a time. The thickened portion which first held the tampon will slip outwardly, the next thickened portion, however, still retaining the tampon in place since part of the pressure has now been relieved. The outward movement of the tampon gives a warning to the patient that the colon should be relieved and that a fresh tampon should be introduced. Slipping of the tampon by one section, however, does not cause loss of the closure entirely if this variation is used.

Figure 3:
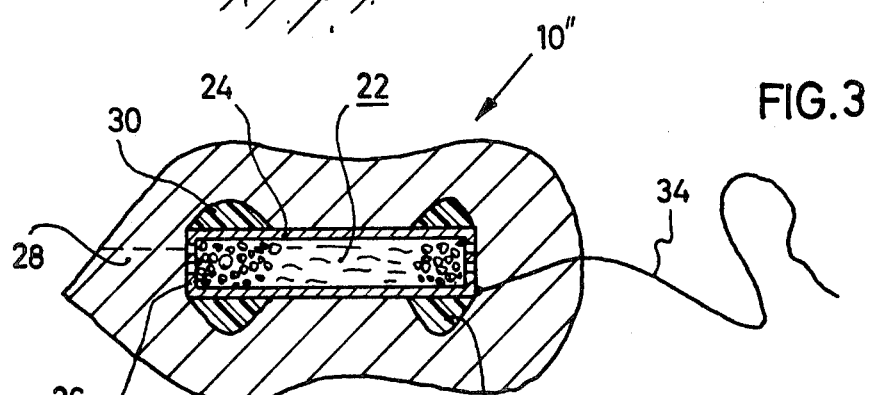
FIG. 3 is a longitudinal section similar to FIG. 1 of another embodiment and showing the arrangement with a core.

The tampon 10" (FIG. 3) is formed with a core 22 made of a plastic tube 24, closed off at the ends with perforated end walls. An odor-suppressing or odor-binding material 26, such as granulated activated charcoal, is placed in the tube 24. The core 22 is surrounded by a cover 28 made of tampon material which, as in the tampon 10 in accordance with FIG. 1, has end sections or portions of greater expanding capability and an intermediate section of less expanding capability. The tampon can be formed in at least a modified hourglass shape already initially, as shown in FIG. 3. The holding capability or plugging or locking capability of the tampon can additionally be enhanced by forming the core 22 with thickened portions 30 at the end, for example by adhering plastic rings on the tube 24 before applying the remainder of the tampon material 28 around the core. The end rings 30 then will shape the tampon 10" as shown in FIG. 3 in the hourglass form, similar to the shape that the tampon will have when wetted, as seen in FIG. 2. If the ends of the tampon 10" are not sufficiently pervious to air or gases, then an axial duct can be formed therein, as schematically illustrated by the broken lines, or the tube 24 can extend close to the front and rear ends of the entire tampon, that is, close to the surface of the surrounding cellular material 28.

Figure 4:
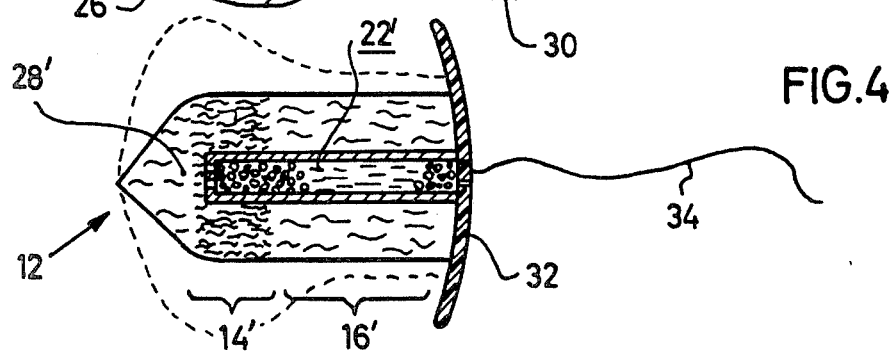
FIG. 4 is a longitudinal sectional view of another embodiment with a closure disk.

For proper seating and operation it is only necessary that the tampon have one inner, plug-like portion adjacent to a constricted portion. FIG. 4 shows an arrangement similar to the embodiment of FIG. 2 with a core 22' in which an odor binder material is included, formed by a tube having perforated end walls, and surrounded by tampon material 28. The tampon in accordance with FIG. 4 has only a single longitudinal portion 14' which can expand, in use, more than the adjacent portion 16', as illustrated, schematically, by the broken lines surrounding the tampon. The portion 14' preferably is made to have more tampon material and higher compressed than the adjacent section 16'. Upon wetting, the section 14' will expand to a greater extent than the adjacent section 16'. The section 16' is located at that side of the section 14' which is away from the pointed end 12 of the tampon. The section 16', if made sufficiently long, ensures reliable seating in combination with the usual constriction right at the exit opening of the artificial ends although only a single thickened section is in the interior of the colon itself. This form of tampon requires, however, a means to prevent slipping of the tampon into the colon; to prevent undesired introduction of the tampon, a soft elastic material, such as a rubber cup 32 is secured to the tampon to close off the exit opening. The cover 32 can be secured to the core 22' and/or to the cover 28' forming the tampon material, that is, compressed cellular material.

The string 34 permits ready removal. In use, a holding belt may also be desirable.

The non-homogeneous characteristics of the tampon, in longitudinal direction, can be obtained by differential quantity of material in the tampon and/or material of different compressibility located next to each other; the cover and/or the core may provide the inhomogeneous characteristics producing the hourglass shape.

The outer surface of the tampon can be knurled or corrugated. For example, circumferential undulations may be provided which, for example, follow each other in wave or undulating form with a spacing of about 1 to 2 cm, peak-to-peak.

In accordance with the feature of the invention, the tampon is made by a compression process, similar to the manufacture of catamenial tampons which expand in use. In order to obtain the differential thickness or density to result in differential expansion of the tampon, a longitudinal body is first compressed with comparatively low compression force so that, looked at longitudinally, it will be generally wave-shaped and have, alternatingly, thickened and thinner regions comprising more and less tampon material, respectively. This intermediate product is then subjected to a stronger compressive force, in radial direction, to smooth out or flatten out the waves until the waviness of the tampon becomes negligible or disappears entirely. The result will be a generally cylindrical tampon which, in sequential longitudinal regions, will have greater and lesser density so that, in use, longitudinal regions will expand differentially.

The tampon can also be made in several parts, for example can be axially or diametrically subdivided into two generally semicylindrical shapes. If a core is to be used, the generally half-cylinders are hollowed to receive the core. The semi-cylindrical elements can then be held together by a resiliently expansible cover such as a tube of gauze or the like which, simultaneously may also form a pull-out tab similar to the string 34.

The cellulose material used may be bound with a wax having a low softening point, so that the compressed tampon material will expand when warmed up by heat from the abdominal wall.

Various changes and modifications may be made within the scope of the inventive concept.

I claim:

1. A non-magnetic closure device for artificial and incontinent natural anal openings, comprising the combination of (a) a holding ring of substantially non-expandng material adapted to be implanted around the anal opening, with (b) a tampon adapted to be removably inserted into the anal opening and there cooperate with the implanted holding ring, said tampon comprising a substantially cylindrical body of cellular material being non-homogenous in the longitudinal direction of the tampon and formed with three longitudinally aligned sections of differential diametrical expansion characteristics when wetted, a first section and a third section having high expansion characteristics when wetted and being separated by an intermediate second section having lesser expansion characteristics when wetted, said second section being adapted to be positioned within said holding ring when the tampon is inserted into the anal opening.

2. The closure device combination according to claim 1 wherein said tampon comprises a substantially axially positioned core of non-magnetic plastic material having the shape of a hollow tube closed at the end with perforated end walls, and an odor binding material located in the space in the interior of the hollow tube.

3. The closure device combination of claim 2, wherein the core is provided with thickened end portions positioned within said first and said third section of the tampon.

4. The closure device combination of claim 1 wherein the first section of the tampon is pointed at the end remote from the other sections.

5. The closure device combination of claim 1 wherein the tampon comprises material expanding upon application of heat.

6. Tampon according to claim 1, further including a cover disk (32) of elastic material located at one end of the elongated body.

7. A non-magnetic closure device for artificial and incontinent natural anal openings, comprising the combination of (a) a holding ring of substantially non-expanding material adapted to be implanted around the anal opening, with (b) an elongated, substantially cylindrical tampon body of a cellular material adapted to be removably inserted into the anal opening and there cooperate with the implanted holding ring, said body being formed with at least two longitudinally aligned sections of alternating differential compressibility, a first section placed adjacent an end of the body adapted to be first when inserted into the anal opening and having lesser compressibility than a second, adjacent section of higher compressibility, a section of the higher compressibility being positioned in alignment with the holding ring when the tampon body is inserted into the anal opening.

8. The closure device of claim 7, wherein any section of lesser compressibility has characteristics of greater expansion when wetted than any section of higher compressibility.

9. The closure device of claim 7, wherein the tampon comprises material expanding upon application of heat.

10. A non-magnetic closure device for artificial and incontinent natural anal openings, comprising the combination of (a) a holding ring of substantially non-expanding material adapted to be implanted around the anal opening, with (b) an elongated, substantially rotational-symmetrical tampon body of cellulose-based material being non-homogenous in its longitudinal direction and adapted to be inserted into the anal opening and there cooperate with the implanted ring, said tampon body having longitudinally aligned alternating sections of differential diametrical expansion characteristics in use, including a first section of high expansion characteristics under at least one of the body influences; heat, moisture: and an adjacent section of lesser expansion characteristics under the same body influences, to provide a plug effect upon insertion of the tampon body into the anal opening with said first section first, said first section prior to being inserted into the anal opening having at least the minimum outer diameter as the minimum diameter of said second section.

11. The closure device combination of claim 10 wherein the tampon body is formed with the internal cavity and a core member is positioned in the cavity.

12. The closure device combination of claim 11 wherein the core member includes an odor binding material.

13. The closure device combination of claim 1 wherein the tampon comprises material expanding upon application of moisture.

* * * * *